(12) United States Patent
Schmidt et al.

(10) Patent No.: US 10,575,744 B2
(45) Date of Patent: Mar. 3, 2020

(54) PERICARDIAL BALLOON MAPPING

(71) Applicant: Medtronic CryoCath LP, Toronto (CA)

(72) Inventors: Megan M. Schmidt, Minneapolis, MN (US); Paul A. Iaizzo, White Bear Lake, MN (US)

(73) Assignee: Medtronic CryoCath LP, Toronto, Ontario ( * ) Notice: Subject to any disclaimer, the term of this patent is extended or adjusted under 35 U.S.C. 154(b) by 413 days.

(21) Appl. No.: 15/441,501

(22) Filed: Feb. 24, 2017

(65) Prior Publication Data
US 2018/0242878 A1 Aug. 30, 2018

(51) Int. Cl.
A61B 5/042 (2006.01)
A61B 5/00 (2006.01)

(52) U.S. Cl.
CPC .......... *A61B 5/0422* (2013.01); *A61B 5/6853* (2013.01)

(58) Field of Classification Search
CPC .................................................. A61B 5/0422
See application file for complete search history.

(56) References Cited

U.S. PATENT DOCUMENTS

| | | | |
|---|---|---|---|
| 4,976,711 A * | 12/1990 | Parins | A61B 18/1492 606/48 |
| 8,406,864 B2 | 3/2013 | Rousso et al. | |
| 8,412,321 B2 | 4/2013 | Gilmour, Jr. et al. | |
| 8,449,442 B2 | 5/2013 | Chin, Jr. et al. | |
| 8,504,133 B2 | 8/2013 | Kordis et al. | |
| 8,513,254 B2 | 8/2013 | Antzelevitch et al. | |
| 8,521,266 B2 | 8/2013 | Narayan et al. | |
| 8,565,851 B2 | 10/2013 | Lau et al. | |
| 8,565,876 B2 | 10/2013 | Armoundas et al. | |
| 8,571,626 B2 | 10/2013 | Lau et al. | |
| 8,594,777 B2 | 11/2013 | Briggs et al. | |
| 8,644,902 B2 | 2/2014 | Kordis et al. | |
| 8,676,303 B2 | 3/2014 | Narayan | |
| 8,682,410 B2 | 3/2014 | Werneth et al. | |
| 8,700,140 B2 | 4/2014 | Narayan et al. | |
| 8,754,087 B2 | 6/2014 | Antzelevitch et al. | |
| 8,812,074 B2 | 8/2014 | Kordis et al. | |
| 8,815,210 B2 | 8/2014 | Wistrand et al. | |
| 8,838,222 B2 | 9/2014 | Narayan et al. | |
| 8,838,223 B2 | 9/2014 | Narayan et al. | |

(Continued)

*Primary Examiner* — Lee S Cohen
(74) *Attorney, Agent, or Firm* — Christopher & Weisberg, P.A.

(57) ABSTRACT

A device, system, and method for mapping myocardial tissue, such as epicardial tissue on the right ventricle. A system for mapping myocardial tissue may include a mapping device having a distal portion that includes a distal assembly sized and configured to be positioned within the pericardial space. The distal assembly may include an expandable shell, at least one inflatable or expandable element within the expandable shell, and a mapping electrode assembly. Inflation or expansion of the at least one inflatable or expandable element, and therefore expansion of the expandable shell, within the pericardial space may provide sufficient force of the mapping electrodes against the myocardial tissue being mapped. The system may also include a delivery sheath with a retention element for controllably retracting the device within the sheath during delivery and removal of the device from the pericardial space.

18 Claims, 10 Drawing Sheets

(56) References Cited

U.S. PATENT DOCUMENTS

| | | |
|---|---|---|
| 8,845,631 B2 | 9/2014 | Werneth et al. |
| 8,868,169 B2 | 10/2014 | Narayan et al. |
| 8,895,753 B2 | 11/2014 | Yoshida et al. |
| 8,920,414 B2 * | 12/2014 | Stone ................ A61B 18/1492 606/41 |
| 8,936,630 B2 | 1/2015 | Denison et al. |
| 8,986,189 B2 | 3/2015 | Chin et al. |
| 9,050,006 B2 | 6/2015 | Narayan et al. |
| 9,055,876 B2 | 6/2015 | Narayan et al. |
| 9,055,877 B2 | 6/2015 | Narayan et al. |
| 9,055,878 B2 | 6/2015 | Narayan et al. |
| 9,056,108 B2 | 6/2015 | Antzelevitch et al. |
| 9,084,590 B2 | 7/2015 | Wittenberger et al. |
| 9,089,269 B2 | 7/2015 | Narayan et al. |
| 9,107,600 B2 | 8/2015 | Narayan et al. |
| 9,119,720 B2 | 9/2015 | Chin et al. |
| 9,126,989 B2 | 9/2015 | Belardinelli et al. |
| 9,149,198 B2 | 10/2015 | Werneth et al. |

\* cited by examiner

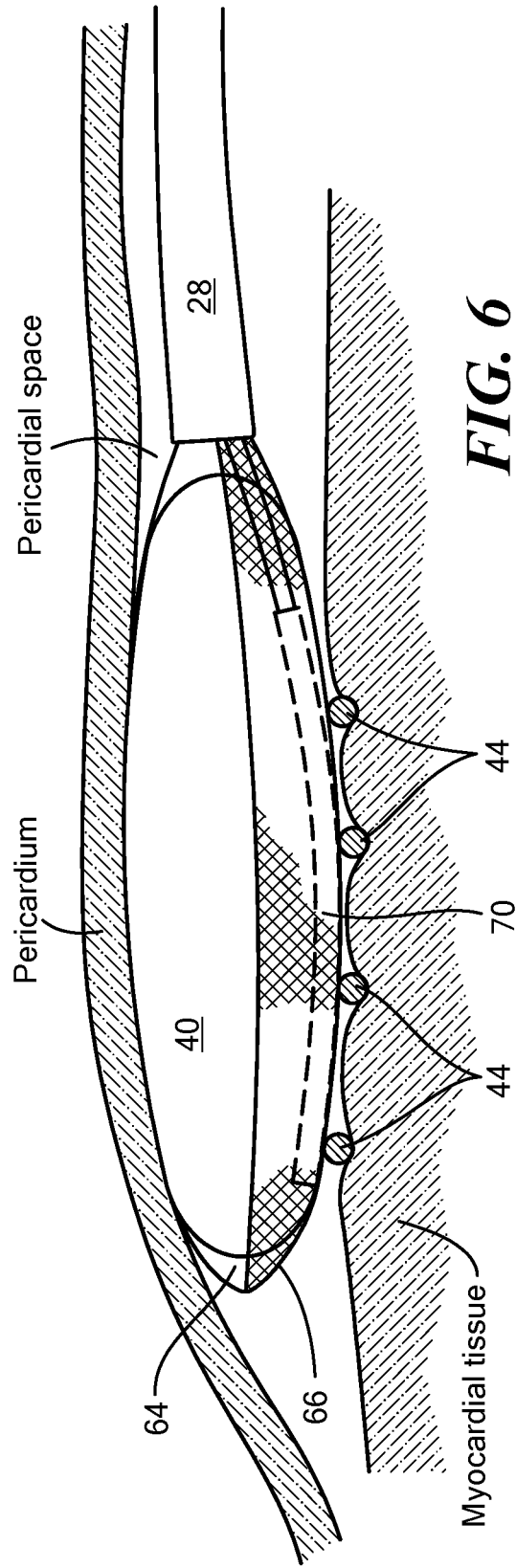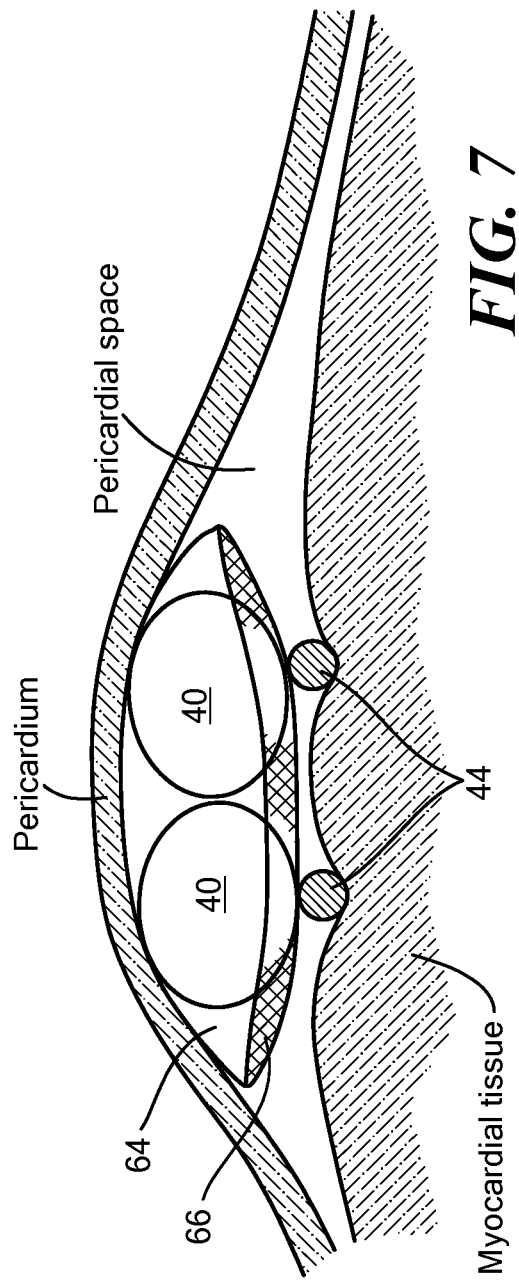

PERICARDIAL BALLOON MAPPING

CROSS-REFERENCE TO RELATED APPLICATION n/a

STATEMENT REGARDING FEDERALLY SPONSORED RESEARCH OR DEVELOPMENT n/a

TECHNICAL FIELD

The present invention relates to a device, system, and method for mapping myocardial tissue.

BACKGROUND

Brugada syndrome is a cardiac rhythm abnormality that can lead to re-entrant ventricular tachycardias and ultimately death, which may be sudden, even in those with structurally normal hearts. In fact, Brugada syndrome often is not associated with any telltale symptoms, so many people who suffer from the condition are unaware of the potential danger.

This syndrome has been associated with genetic mutations in, most commonly, the gene SCN5A, which is involved in the creation of myocardial sodium ion channels. Ion channels transport sodium ions into heart muscle cells and are essential for maintaining normal cardiac rhythm. Mutations in this gene can lead to the development of Brugada syndrome, which may be associated with sodium channel abnormalities and early repolarization in the epicardium of the right ventricle.

Brugada syndrome may be treated with preventive measures including avoiding certain medications and reducing fever, and, in some cases, may be managed with the use of an implantable cardioverter-defibrillator (ICD). The key to successful treatment, however, is identifying the presence of the condition. Electrogram recordings are typically used for cardiac mapping, but this data does not provide information about ion channels and overall viability other than the amplitude of the myocardial electrical activity, and even this can depend on contact force between the recording electrode and the myocardial tissue being mapped.

SUMMARY

The present invention advantageously provides a device, system, and method for mapping myocardial tissue, such as epicardial tissue on the right ventricle. In one embodiment, a device includes a distal assembly having an outer shell, at least one inflatable element within the outer shell, and an electrode assembly at least partially within the outer shell proximate the at least one inflatable element. In one aspect of the embodiment, the electrode assembly includes a plurality of mapping electrodes.

In one aspect of the embodiment, the electrode assembly includes a central shaft, a plurality of carrier arms coupled to the central shaft, and a plurality of electrodes, at least one of the plurality of electrodes being coupled to each of the plurality of carrier arms. In one aspect of the embodiment, each of the plurality of carrier arms has a first end and a second end opposite the first end, the first end being coupled to the central shaft and the second end being coupled to the at least one of the plurality of electrodes. In one aspect of the embodiment, the second end of each of the plurality of carrier arms is coupled to at least two of the plurality of electrodes.

In one aspect of the embodiment, the plurality of carrier arms includes a first set of carrier arms and a second set of carrier arms, the central shaft includes a first side and a second side, the first set of carrier arms being coupled to the first side of the central shaft and the second set of carrier arms being coupled to the second side of the central shaft. In one aspect of the embodiment, each carrier arm of the first set of carrier arms is at least substantially opposite a corresponding carrier arm of the second set of carrier arms. In another aspect of the embodiment, the first set of carrier arms alternates with the second set of carrier arms.

In one aspect of the embodiment, the outer shell includes a first portion composed of a first material and a second portion composed of a second material. In one aspect of the embodiment, the first material is a semi-compliant material. In one aspect of the embodiment, the second material is a mesh.

In one aspect of the embodiment, the at least one inflatable element is proximate the first portion and the electrode assembly is proximate the second portion.

In one aspect of the embodiment, the outer shell includes an outer surface and an inner chamber, the central shaft and the plurality of carrier arms being located within the inner chamber of the outer shell and the plurality of electrodes at least partially extending from the outer surface of the outer shell second portion.

In one aspect of the embodiment, the device further includes an elongate body including a distal portion, a proximal portion opposite the distal portion, and a lumen extending therebetween, the outer shell being coupled to the elongate body distal portion. In one aspect of the embodiment, each of the at least one inflatable element is in fluid communication with an inflation conduit located at least partially within the elongate body lumen.

In one aspect of the embodiment, the device further includes a sheath including a distal portion, a proximal portion opposite the distal portion, and a lumen extending therebetween, a retention element coupled to the sheath distal portion, and a stopper located distal to the distal assembly, the stopper being engageable with the retention element. In one aspect of the embodiment, the retention element includes an annular element and at least one tether, each of the at least one tether having a first end coupled to the sheath distal portion and a second end coupled to the annular element, the stopper being engageable with the annular element when the distal assembly is retracted within the sheath lumen.

In one embodiment, a mapping system includes: an elongate body including a distal portion, a proximal portion opposite the distal portion, and a lumen extending therebetween; an outer shell coupled to the distal portion of the elongate body, the outer shell having a first portion composed of a first material and a second portion composed of a second material; at least one inflatable element within the outer shell and proximate the first portion of the outer shell; an electrode assembly at least partially within the outer shell between the at least one inflatable element and the second portion of the outer shell, the electrode assembly having: a central shaft at least partially disposed with the lumen of the elongate body; a plurality of carrier arms, each of the plurality of carrier arms having a first end and a second end opposite the first end, the first end being coupled to the central shaft; and a plurality of mapping electrodes, at least one of the plurality of mapping electrodes being coupled to the second end of each of the plurality of carrier arms. The system also includes: a sheath including a distal portion, a proximal portion opposite the distal portion, and a lumen extending therebetween; a retention element coupled to the sheath distal portion; and a stopper located distal to the distal assembly, the stopper being engageable with the retention element.

In one aspect of the embodiment, the system further includes a control unit including processing circuitry configured to receive from the plurality of mapping electrodes mapping signals recorded from an area of tissue, the processing circuitry being programmed to: compare the recorded mapping signals to mapping signals of healthy tissue; and determine if the comparison indicates the presence of Brugada syndrome in the area of tissue.

In one embodiment, a method for mapping myocardial tissue may include: positioning a distal assembly of a mapping device within a pericardial space between a pericardium and the myocardial tissue, the distal assembly being collapsed, the distal assembly including: an outer shell having a first portion and a second portion, the first portion of the outer shell being in contact with the pericardium when the mapping device is positioned within the pericardial space and the second portion of the outer shell being in contact with the myocardial tissue when the mapping device is positioned within the pericardial space; at least one inflatable element within the outer shell and proximate the first portion of the outer shell; and an electrode assembly at least partially within the outer shell proximate the at second portion of the outer shell, the electrode assembly having a plurality of mapping electrodes; expanding the outer shell by inflating the at least one inflatable element, expansion of the outer shell exerting a force against electrode assembly to enhance contact between the plurality of mapping electrodes and the myocardial tissue; and recording monophasic action potentials from the myocardial tissue.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 6 shows a side view of the distal portion of the mapping device between the epicardium and the myocardium of a heart;

FIG. 7 shows a front view of the distal portion of the mapping device between the epicardium and the myocardium of a heart;

DETAILED DESCRIPTION

Figure 1:
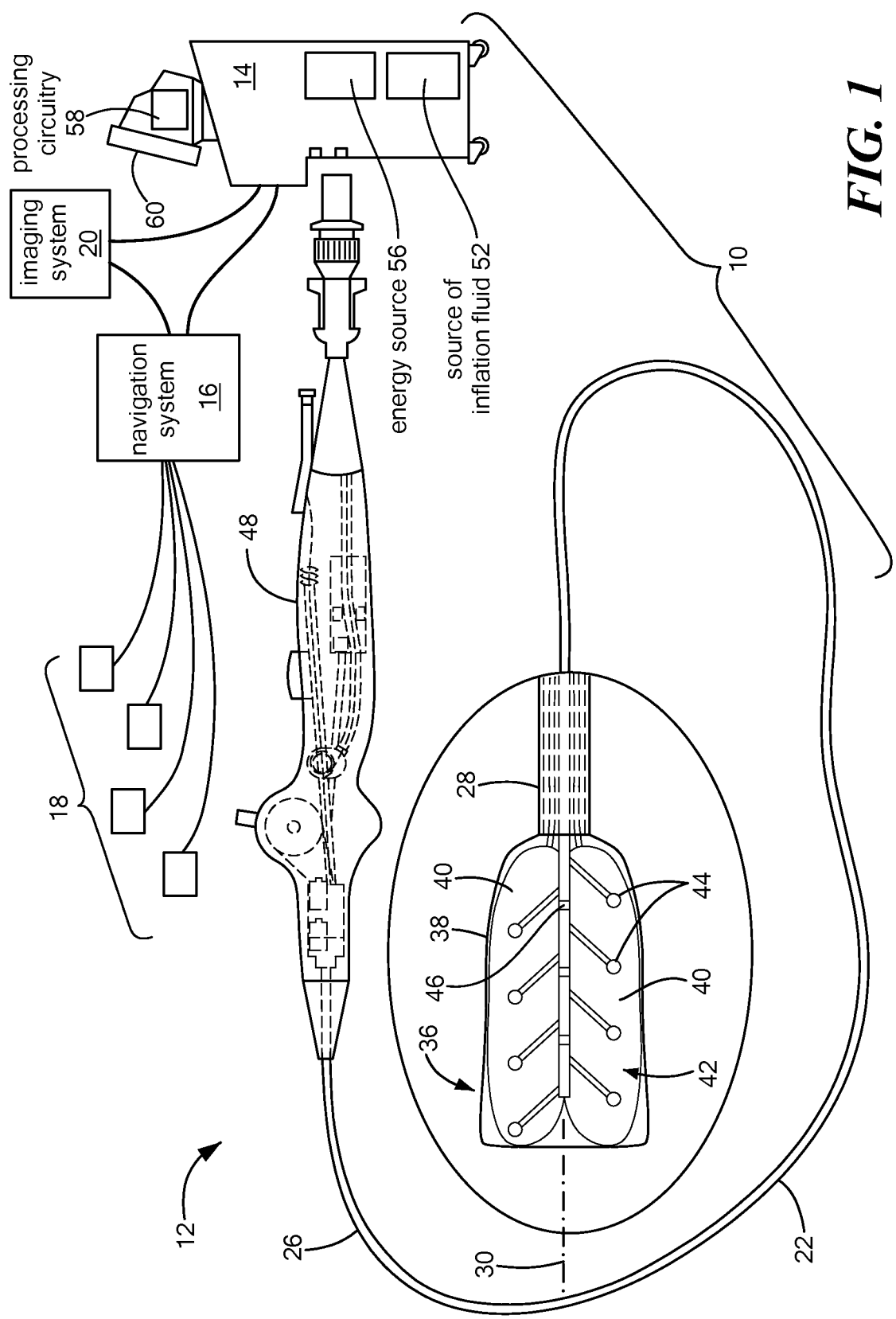
FIG. 1 shows an exemplary medical system including a mapping device for recording monophasic action potentials.

The systems and methods disclosed herein are for the mapping of myocardial tissue, such as epicardial tissue on the right ventricle. For example, a system for mapping myocardial tissue may include a mapping device having a distal portion that includes a distal assembly sized and configured to be positioned within the pericardial space. The distal assembly may include an expandable shell, at least one inflatable or expandable element within the expandable shell, and a mapping electrode assembly. Inflation or expansion of the at least one inflatable or expandable element, and therefore expansion of the expandable shell, within the pericardial space may provide sufficient force of the mapping electrodes against the myocardial tissue being mapped.

Before describing in detail exemplary embodiments that are in accordance with the disclosure, it is noted that components have been represented where appropriate by conventional symbols in drawings, showing only those specific details that are pertinent to understanding the embodiments of the disclosure so as not to obscure the disclosure with details that will be readily apparent to those of ordinary skill in the art having the benefit of the description herein.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Referring now to the drawing figures in which like reference designations refer to like elements, an embodiment of a medical system is shown in FIG. 1, generally designated as "10." The device components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein are not necessarily exclusive of each other and may be included in a variety of different combinations or configurations without departing from the scope and spirit of the invention.

One embodiment of the system 10 may generally include a mapping device 12 in communication with a control unit 14. Optionally, the system 10 may also include a navigation system 16, a treatment device (not shown) in communication with the navigation system 16 having surface electrodes 18 and/or the control unit 14, and an imaging system 20 for obtaining images of anatomical features within a patient.

Although the system 10 may include a separate treatment device, the mapping device 12 may function as a treatment and mapping device. The medical device 12 may include an elongate body 22 passable through a patient's vasculature and/or proximate to a tissue region for diagnosis or treatment. For example, the device 12 may be a catheter that can access the pericardial space, such as through sub-xiphoid access. The elongate body 22 may define a proximal portion 26, a distal portion 28, and a longitudinal axis 30, and may further include one or more lumens disposed within the elongate body 22 that provide mechanical, electrical, and/or fluid communication between the elongate body proximal portion 26 and the elongate body distal portion 28. For example, the elongate body 22 may include a central lumen 32.

As is discussed in more detail below, the mapping device 12 may include a distal assembly 36 at or coupled to the elongate body distal portion 28. The mapping assembly 36 may generally include an expandable shell 38, at least one expandable element 40, and a mapping electrode assembly 42 including a plurality of mapping electrodes 44 and at least one indifferent electrode 46. Each mapping electrode 44 may have an associated indifferent electrode 46, although one indifferent electrode 46 may be associated with more than one electrode 44. Indifferent electrodes are not required when unipolar MAPs are recorded. The plurality of mapping electrodes 44 may be in communication with the control unit 14 such that mapping signals (for example, monophasic action potentials, or MAPs) may be transmitted from the mapping electrodes 44 to the control unit 14 for evaluation, visualization, recordation, further processing, or the like. If the system 10 includes a navigation system 16, the plurality of mapping electrodes 44 may be used by the navigation system 16 to visualize the device 12 on a control unit display and/or a navigation system display. Further, if the device 12 functions as a treatment and mapping device, the device may also include one or more treatment elements (not shown) and/or each mapping electrode 44 may be electrically and/or thermally conductive and in communication with a power source for conveying an electrical signal, current, or voltage to a designated tissue region and/or for measuring, recording, receiving, receiving, assessing, or otherwise using one or more electrical properties or characteristics of surrounding tissue or other electrodes. The treatment element(s) and/or electrodes 44 may be configured in a myriad of different geometric configurations or controllably deployable shapes, and may also vary in number to suit a particular application, targeted tissue structure or physiological feature.

Although not shown, the system 10 may include one or more sensors to monitor the operating parameters throughout the system, including for example, pressure, temperature, flow rates, volume, power delivery, impedance, or the like in the control unit 14 and/or the mapping device 12, in addition to monitoring, recording or otherwise conveying measurements or conditions within the device 12 or the ambient environment at the distal portion of the device 12. The sensor(s) may be in communication with the control unit 14 for initiating or triggering one or more alerts or therapeutic delivery modifications during operation of the device 12. One or more valves, controllers, or the like may be in communication with the sensor(s) to provide for the controlled dispersion or circulation of fluid through the lumens/fluid paths of the device. Such valves, controllers, or the like may be located in a portion of the device and/or in the control unit 14.

The device 12 may include a handle 48 coupled to the elongate body proximal portion 26. The handle 48 may include circuitry for identification and/or use in controlling of the medical device 16 or another component of the system. Additionally, the handle 48 may also include connectors that are mateable to the control unit 14 to establish communication between the device 12 and one or more components or portions of the control unit 14. The handle 48 may also include one or more actuation or control features that allow a user to control, deflect, steer, or otherwise manipulate a distal portion of the device 12 from the proximal portion of the medical device 16. For example, the handle 48 may include one or more components such as a lever or knob for manipulating the elongate body 22 and/or additional components of the device 12.

As used herein, the term "control unit 14" for simplicity may include any system components that are not part of the mapping device 12 itself, and may include other components such as the navigation system 16 and the imaging system 20, regardless of whether the component is physically located within or external to the control unit 14. If the system includes a treatment device, and/or if the device 12 functions as a mapping and treatment device, the control unit 14 may include one or more components for the delivery of one or more energy modalities for which the system is used. For example, if the system 10 is used to deliver cryotherapy, the control unit 14 may include a supply of a fluid such as a coolant, cryogenic refrigerant, or the like, an exhaust or scavenging system for recovering or venting expended fluid for re-use or disposal, as well as various control mechanisms. Additionally, the control unit 14 may include a source of inflation fluid 52 for inflating the at least one expandable element 40, as is discussed in more detail below. In addition to providing an exhaust function for the fluid or coolant supply, the control unit 14 may also include pumps, valves, controllers or the like to recover and/or re-circulate fluid delivered to the handle 48, the elongate body 22, and/or the fluid pathways of the device 12 or other devices of the system 10. Further, a vacuum pump in the control unit 14 may create a low-pressure environment in one or more conduits within the device(s) so that fluid is drawn into the conduit(s)/lumen(s) of the elongate body, away from the distal portion and towards the proximal portion of the elongate body. Additionally or alternatively, the control 14 unit may include an energy source 56 as a treatment or diagnostic mechanism in communication with the mapping electrodes 44 and, optionally, treatment device. As a non-limiting example, the energy source 56 may provide electrical currents to the distal assembly 36 for the collection of MAPs, as discussed in more detail below.

The control unit 14 may further include one or more controllers, software modules, and/or processing circuitry 58 configured to execute instructions or algorithms to provide for the automated operation and performance of the features, sequences, calculations, or procedures described herein and/or required for a given medical procedure. In one embodiment, the processing circuitry 58 may include a processor and a memory. The memory may be in electrical communication with the processor and have instructions that, when executed by the processor, configure the processor to receive, process, or otherwise use signals from the device 12. Further, the control unit 14 may include one or more user input devices, controllers, and displays 60 for collecting and conveying information from and to the user.

Referring now to FIGS. 2-7, the distal assembly is shown in greater detail. As noted above, the distal assembly 36 may include an expandable outer shell 38 and at least one expandable element 40 and mapping electrode assembly 42 within the expandable shell 38. The distal assembly 36 may be coupled to the elongate body distal portion 28 and may be retractable within a sheath, as described in more detail below. In one configuration, the outer shell 38 may be coupled to the elongate body distal portion 28 and may at least substantially or entirely enclose the at least one expandable element 40 and the mapping electrode assembly 42. The outer shell 38 may include a first portion 64 composed of a first material that is attached to, manufactured with, or integrated with a second portion 66 composed of a second material. As a non-limiting example, the first material maybe a semi-compliant material, such as those commonly used for cryoballoons or ablation balloons. Further, the first material may itself be hydrophobic and/or may be coated with a hydrophobic material. The second material may be a mesh that allows for the dissipation of heat, fluid (for example, an inflation fluid used to expand the at least one expandable element 40), or other materials from within the outer shell 38. As a non-limiting example, the mesh may include a plurality of interwoven fibers composed of Nitinol wires, or wires or fibers of another suitable conductive, non-conductive, and/or shape-memory material. The mesh may act as a base for the wiring and fixation of the electrodes 44. Optionally, the mesh may be at least partially composed of, or may otherwise support or include, the electrode wires. The mesh may also provide structural support to the bottom surface of the outer shell 38. When the device is in use, the first portion 64 may be positioned proximate the target tissue whereas the second portion 66 may be positioned proximate the pericardium.

The mapping electrode assembly 42 may include a central shaft 70 and a plurality of mapping electrode carrier arms 72. The carrier arms 72 may extend from the central shaft 70 by an angle of, for example, between approximately 90° and approximately 20° (or approximately 160° depending on the direction of measurement) from the longitudinal axis of the central shaft 70. The carrier arms 72 may be coupled to or attached to the shaft 70 by any suitable method, such as by welding, thermal bonding, chemical bonding, mechanical connection, or the like. Alternatively, the central shaft 70 and the carrier arms 72 may be manufactured as a single integrated device component. The central shaft 70 and carrier arms 72 may be composed of any suitable material that is rigid or stiff enough to support the mapping electrodes 44. As a non-limiting example, the central shaft 70 and carrier arms 72 may be composed of a plastic or metal or combination thereof, and they may be composed of the same or different materials. Further, the central shaft 70 and the carrier arms 72 may each be at least substantially linear, as shown in the figures; however, it will be understood that they may have any size, shape, or configuration suitable for performing the mapping functionality described herein.

Figure 2:
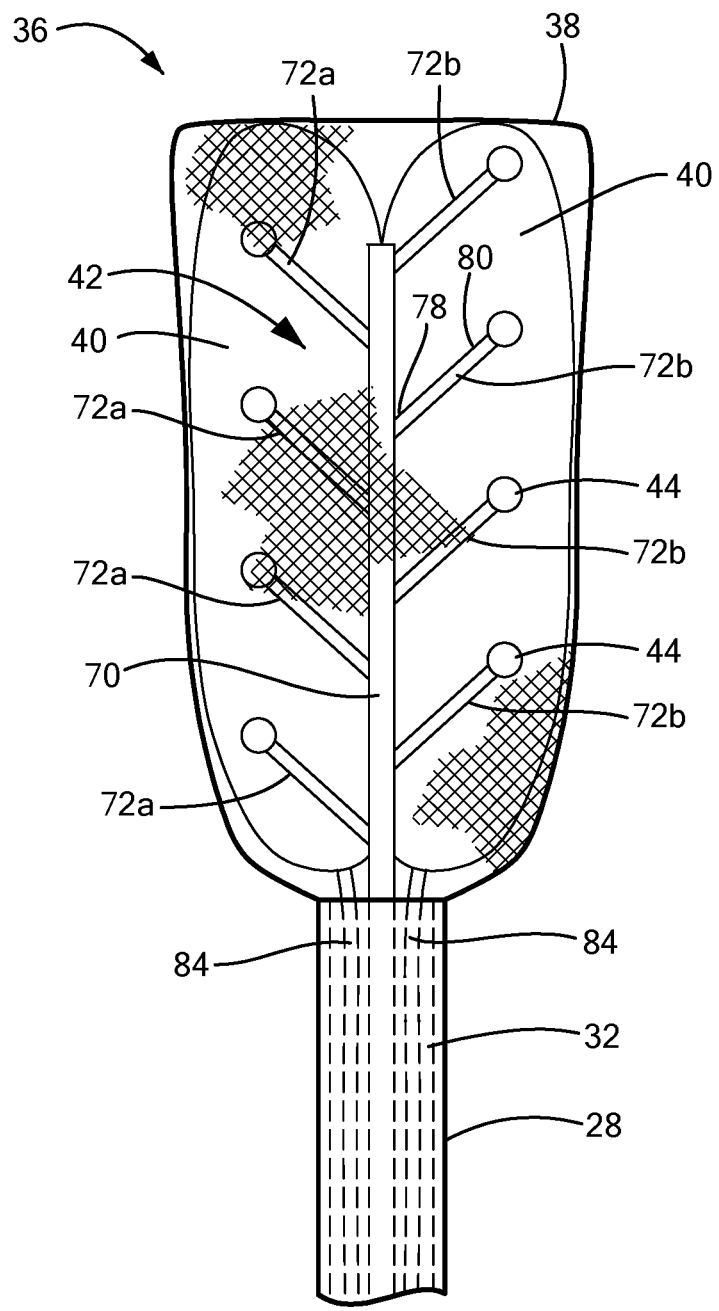
FIG. 2 shows a bottom view of a first configuration of a distal portion of the mapping device.
Figure 3:
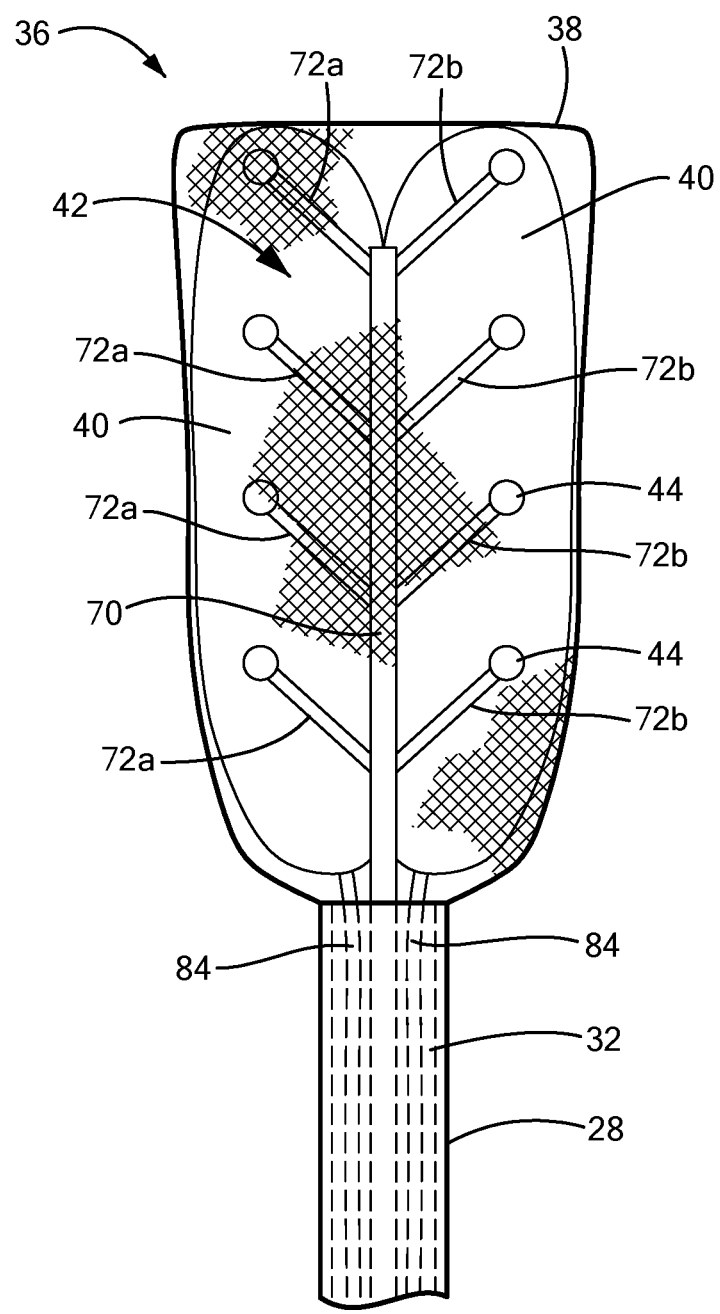
FIG. 3 shows a bottom view of a second configuration of a distal portion of the mapping device.
Figure 4:
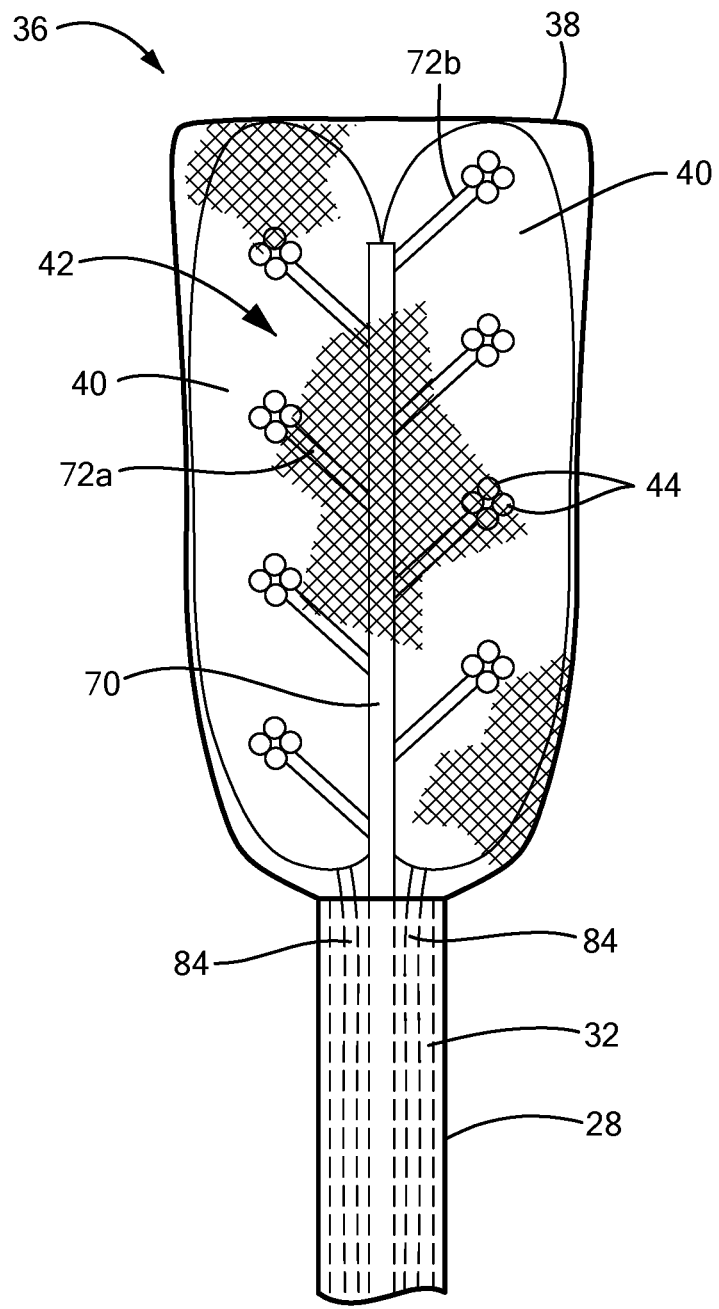
FIG. 4 shows a bottom view of a third configuration of a distal portion of the mapping device.
Figure 5:
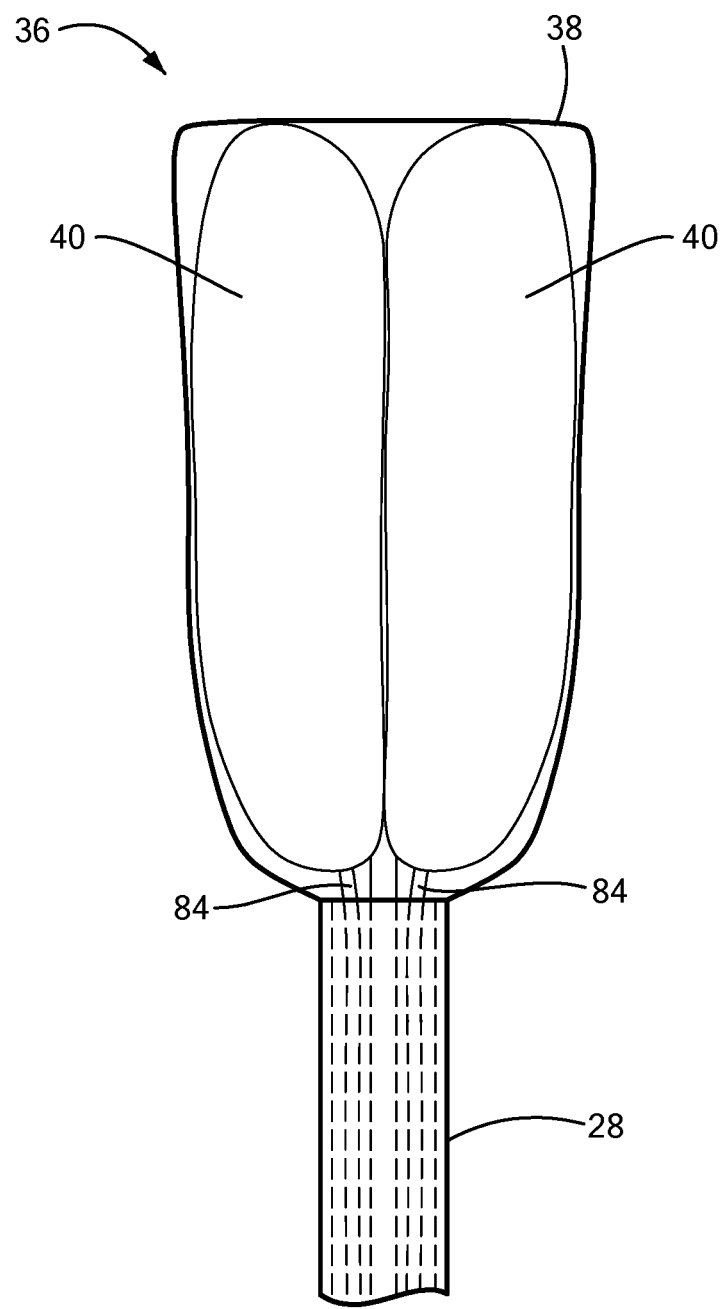
FIG. 5 shows a top view of the distal portion of the mapping device.

The mapping electrode assembly 42 may include any number of carrier arms 72, even though eight carrier arms 72 are shown in the figures as a non-limiting example. The carrier arms 72 may be equally divided into a first set of carrier arms 72*a* coupled to or integrated with a first side of the central shaft 70 and a second set of carrier arms 72*b* coupled to or integrated with a second side of the central shaft 70. In one embodiment, the first set of carrier arms 72*a* may alternate with the second set of carrier arms (for example, as shown in FIGS. 1, 2, and 4). In another embodiment, each carrier arm of the first set of carrier arms 72*a* may be at least substantially opposite a corresponding carrier arm of the second set of carrier arms 72*b* (for example, as shown in FIG. 3). The central shaft 70 may have any suitable cross-sectional shape, such as a circular, oval rectangular, square, or polygonal cross-sectional shape. Despite the shape, however, the first side and the second side of the central shaft 70 may be approximately 180° (±15°) from each other.

Each carrier arm 72 may include a first (or proximal) end 78 that meets or is attached to the central shaft 70 and a second (or distal) end 80 opposite the first end 78. The second end 80 of each carrier arm 72 may bear or be coupled to at least one mapping electrode 44. The length of each carrier arm 72 may be chosen such that each of the plurality of mapping electrodes 44 is located at a desired distance from the central shat 70. In the embodiment shown in FIGS. 1-3, each carrier arm 72 may include a single mapping electrode 44 at the distal end 80. In an alternative embodiment, each carrier arm 72 may include a plurality of mapping electrodes 44, such as in a cluster configuration. In a non-limiting example, each carrier arm 72 may include a cluster of four mapping electrodes (for example, as shown in FIG. 4). However, it will be understood that the cluster may have any number of electrodes, and may include as few as two electrodes 44. The multi-electrode clusters may improve stability and contact between the electrodes and the tissue being mapped, and thereby may improve mapping signal quality.

The mapping electrodes 44 may have any suitable size, shape, or configuration. As a non-limiting example, the electrodes 44 may be at least substantially spherical with a rounded surface on the tissue-facing side of the electrode. Further, the mapping electrodes 44 may be composed of an electrically conductive material, such as gold, tantalum, iridium, nickel, metal alloys, or the like. Each mapping electrode 44 may be in electrical communication with the control unit 14 for transmitting mapping signals to the control unit 14 for recordation, processing, and/or communication to or with the user. Further, each mapping electrode 44 may extend or pass through the mesh second portion 66 of the outer shell 38 such that each mapping electrode 44 is exposed on an outer surface of the outer shell 38. In this way, the mapping electrodes 44 may be in direct contact with the tissue to be mapped.

The distal assembly 36 may further include one or more expandable elements 40 within the outer shell 38. The expandable elements 40 may be located between the mapping electrode assembly 42 and the outer shell first portion 64, such that when the expandable elements 40 are inflated, the expandable elements 40 exert pressure against the mapping electrode assembly 42, thereby enhancing contact between the mapping electrodes 44 and the tissue being mapped. This pressure is facilitated not only by inflation and expansion of the expandable elements 40 within the outer shell 38, but also by the distal assembly's being located between the myocardial tissue and the pericardium (that is, the pericardium may exert a force on the distal assembly 36, pushing it against the myocardial tissue). As the quality of MAPs may depend on the amount of pressure exerted on the mapped tissue by the mapping electrodes, this distal assembly configuration may enhance the quality of recorded MAPs.

Each of the expandable elements 40 may be coupled to a fluid conduit 84 (which may also be referred to as an inflation conduit) that is in fluid communication with the source of inflation fluid 52. The inflation fluid may be any suitable fluid, including but not limited to air, nitrogen, cyrogenic fluid, saline, water, or the like. Additionally or alternatively, the inflation fluid may be a gel.

Figure 8:
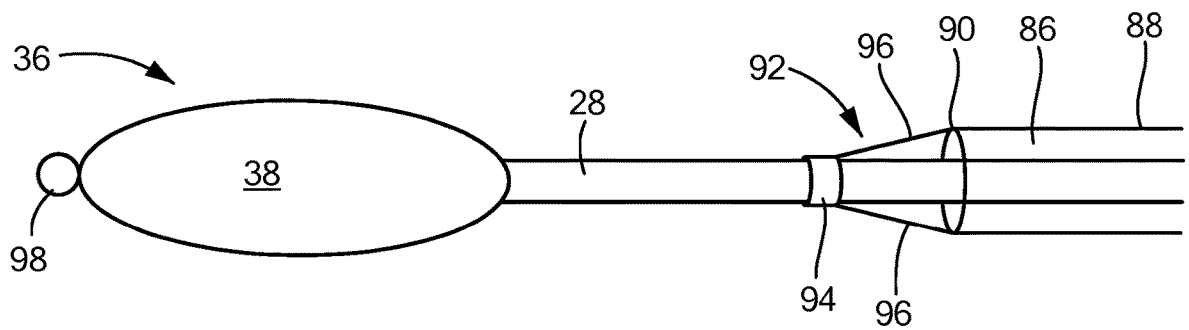
FIGS. 8-10 show a method of retracting the distal portion of the mapping device within a sheath.
Figure 9:
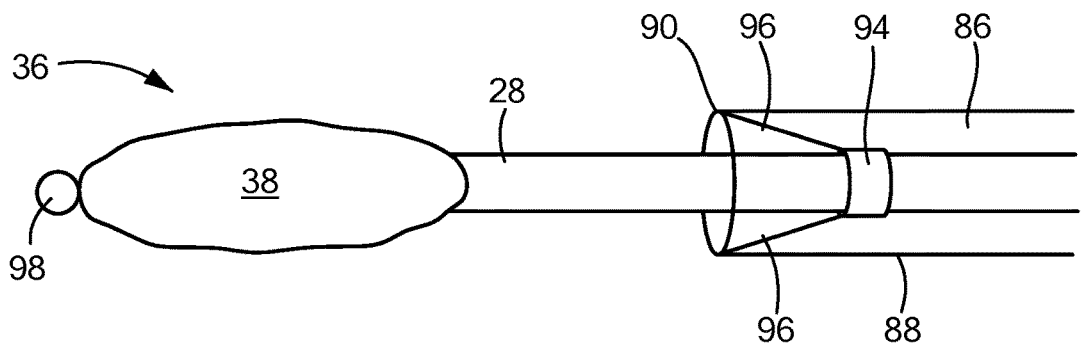
Figure 10:
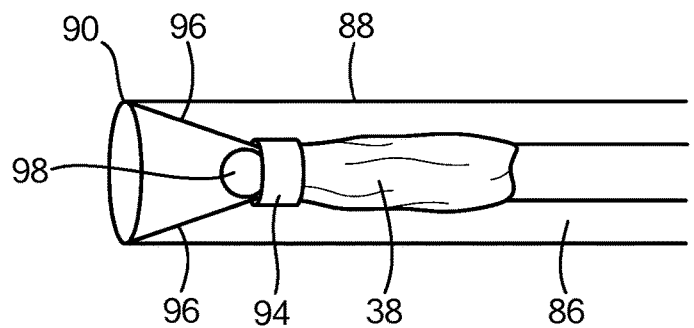

Referring now to FIGS. 8-10, a further embodiment of the mapping device is shown. In this embodiment, the distal assembly 36 may be configured to be collapsed and the elongate body 22 with distal assembly 36 controllably retracted within a central lumen 86 of a sheath 88 to facilitate navigation of the device to and from the treatment site. For example, the sheath 88 may include a distal portion 90, a proximal portion opposite the distal portion, and a lumen 86 extending therebetween. The expandable elements 40 may be uninflated and collapsed, thereby collapsing the outer shell 38, and the elongate body 22 with distal assembly 36 may be at least partially retracted within the sheath central lumen 86 when the device is in a delivery or removal configuration. Although not shown, it will be understood that the device shown in FIGS. 1-7 may also be delivered to and removed from a target site using a sheath.

The device 12 may include a retention element 92 coupled to the sheath 88 that limits retraction of the distal assembly 36 to a predetermined distance within the elongate body 22. For example, the retention element 92 may include an annular element 94, such as a rubber ring, that is sized and configured such that the elongate body 22 may freely move through the aperture of the annular element 94 as the elongate body 22 and distal assembly 36 are extended from and retracted into the sheath 88. The retention element 92 may further include one or more tethers 96 having a first end coupled to the distal end of the sheath 88 (for example, to the distalmost end of the sheath) and a second end coupled to the annular element 94.

The device 12 may include or define a stopper 98 that has an outer diameter that is greater than the inner diameter of the annular element 94. For example, the stopper 98 may be at a location that is immediately distal to the distal end of the outer shell 38. Thus, when the distal assembly 36 is retracted into the sheath 88, the stopper 98 is unable to pass through the aperture of the annular element 94, and the distal assembly 36 is prevented from being further retracted within the sheath 88. The annular element 94 may be freely movable within the sheath 88, but its movement may be limited by the tethers 96, as shown in FIGS. 8-10.

In use, the device 12 may be maneuvered to a target mapping site. For example, if the target mapping site is within the pericardial space, the device 12 may be positioned between the pericardium and the outer surface of the heart through sub-xiphoid pericardial access. During delivery of the device 12 to the target mapping site, the at least one expandable element 40 may be deflated and collapsed, thereby also collapsing the outer shell 38. Additionally, if the device 12 includes a retractable distal assembly 36 as shown in FIGS. 8-10, the distal assembly 36 may also be retracted within the elongate body lumen 32.

Once at the target mapping site, the at least one expandable element 40 may be inflated by delivering fluid to the inner chamber of each expandable element 40 from the inflation fluid source 52. The inflation fluid may be continuously circulated within the expandable element(s) 40 during the procedure, or one or more valves within the fluid flow paths of the system may be used to prevent fluid from exiting the expandable element(s) once they are inflated. As discussed above, inflation of the expandable element(s) may likewise expand the outer shell 38 and may exert a force against the mapping electrodes 44, pushing them against the myocardial tissue to enhance contact between the mapping electrodes 44 and the myocardial tissue (this may be referred to as creating a contact force against the target tissue). As the outer shell 38 continues to expand, the increased pressure of the pericardium against the outer shell 38 may also contribute to the force exerted against the mapping electrodes 44 and target tissue. This pressure may cause the mapping electrodes 44 to extend through the mesh of the outer shell second portion 66. Alternatively, the distal assembly 36 may be manufactured such that the mapping electrodes 44 are permanently located on or proximate an outer surface of the mesh of the second portion 66, whereas the rest of the mapping electrode assembly 42 remains within the interior chamber of the outer shell 38.

Figure 11:
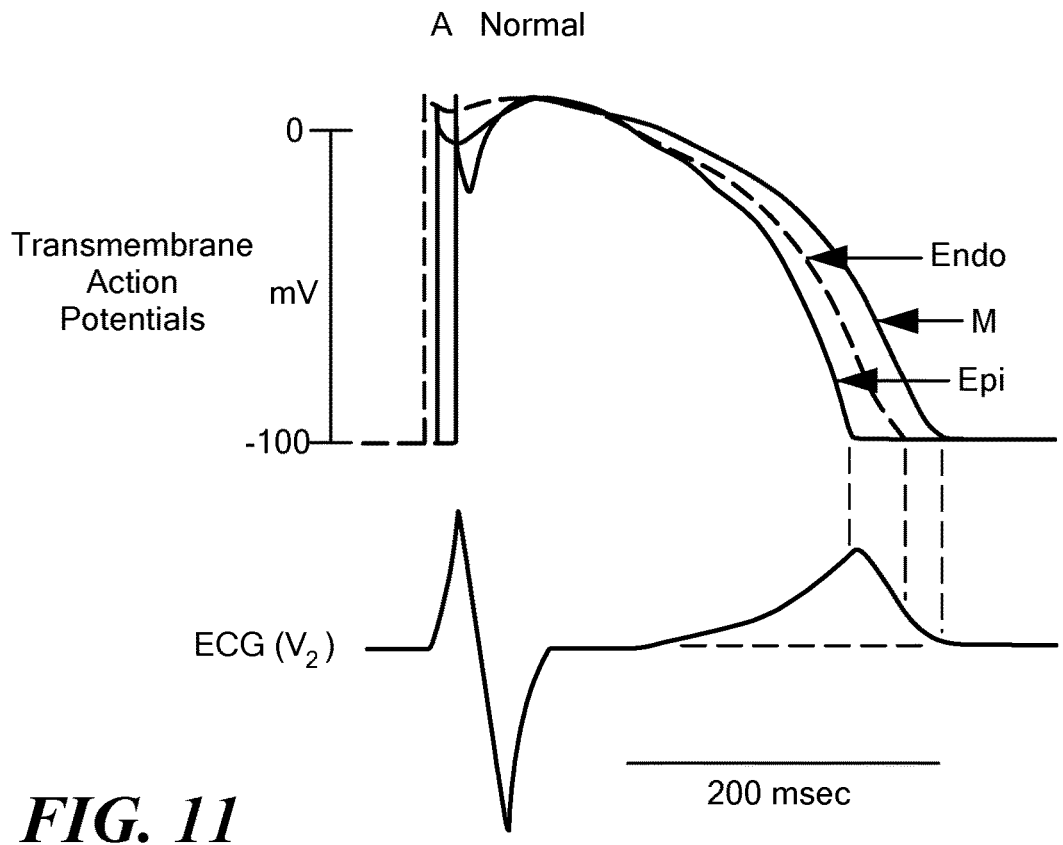
FIG. 11 shows an exemplary normal transmembrane action potential of a myocardial cell with a corresponding electrocardiogram.
Figure 12:
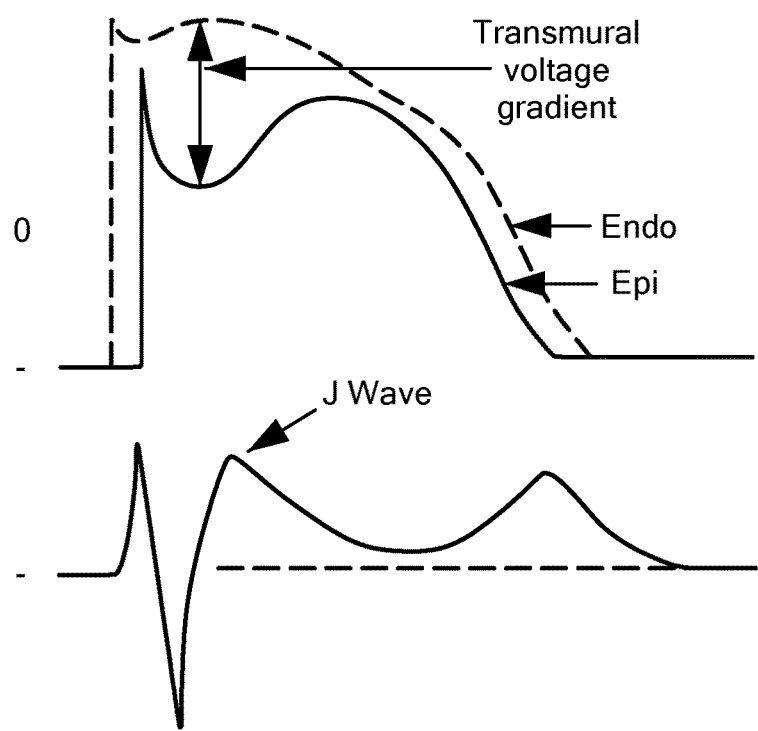
FIGS. 12-15 show exemplary transmembrane action potentials of a myocardial cell with corresponding electrocardiograms associated with Brugada syndrome.
Figure 13:
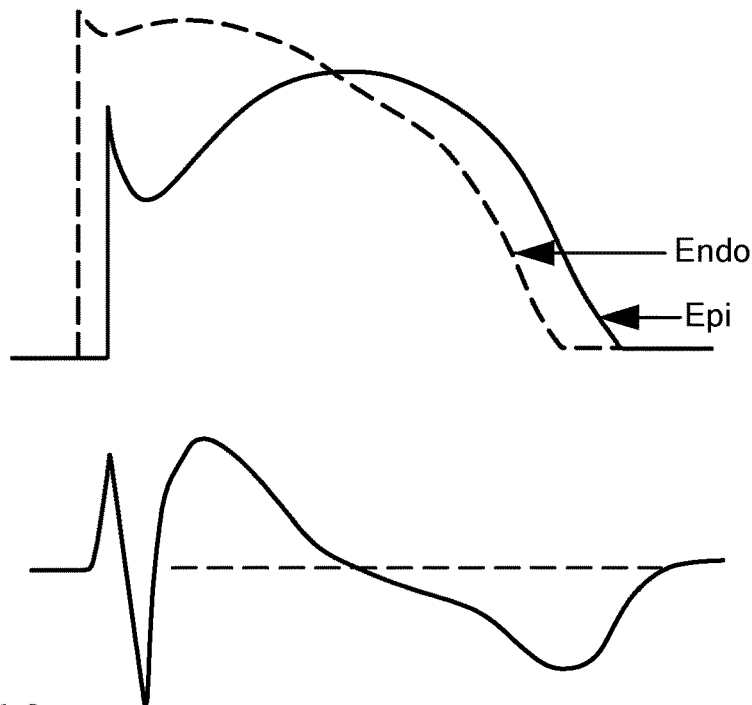
Figure 14:
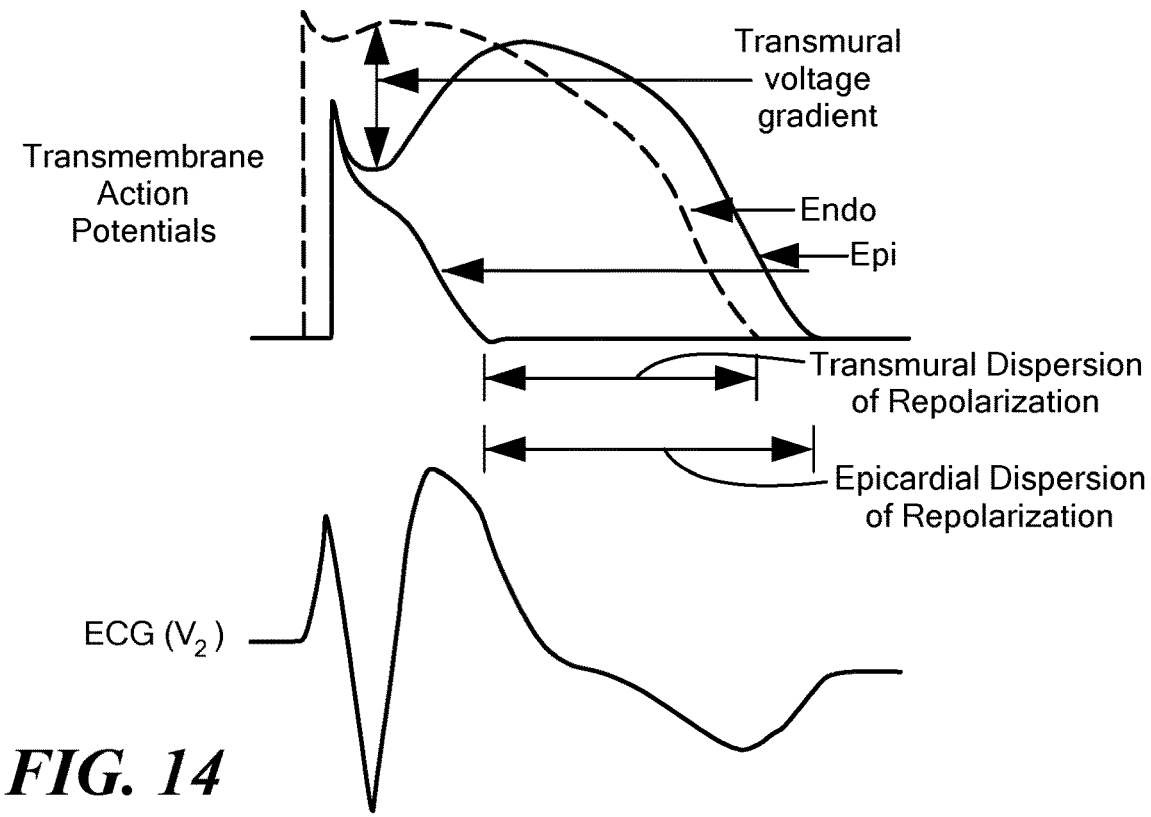
Figure 15:
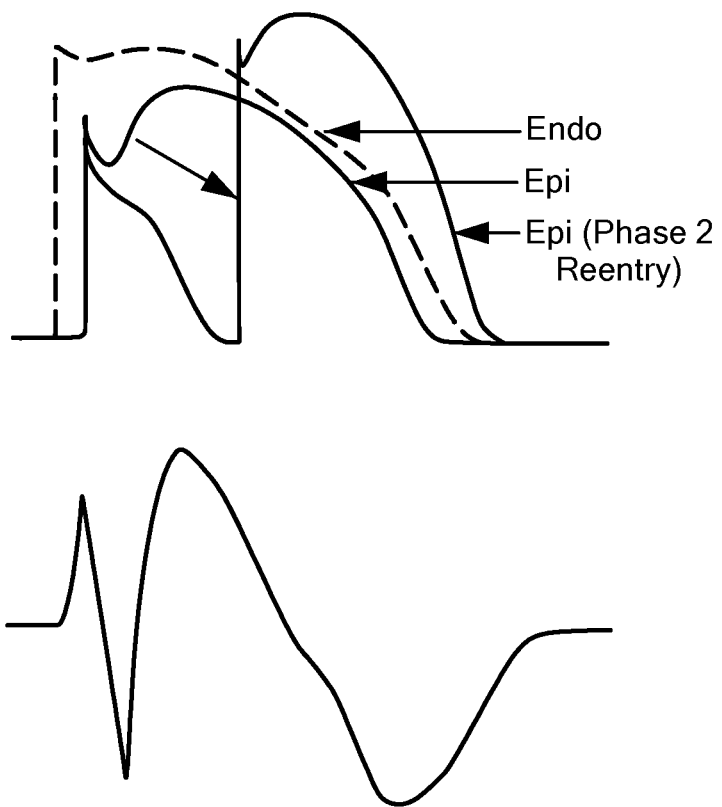

Once the outer shell 38 is fully expanded, or expanded to a desired degree (such that a desired force is exerted by the mapping electrodes 44 against the target tissue), mapping signals may be recorded from each of the mapping electrodes 44, or at least those mapping electrodes that are in contact with the target tissue, and/or the indifferent electrode(s) 46. As a non-limiting example, MAPs may be recorded by the mapping electrodes 44 and transmitted to the processing circuitry 58 of the control unit 14. The processing circuitry 58 may then analyze the mapping signals by comparing the recorded signals to known "normal" MAPs (that is, MAPs of healthy myocardial cells functioning normally) and, optionally, "normal" electrocardiograms (that is, electrocardiograms of healthy myocardial cells functioning normally). A MAP is a representation of the transmembrane action potential measured from a location exterior to the cell. FIG. 11 shows a transmembrane action potential and associated electrocardiogram of a "normal" myocardial cell.

FIGS. 12-15 show exemplary MAPs of a myocardial cell and corresponding electrocardiograms that are indicative of Brugada syndrome. The processing circuitry 58 may determine that recorded signals (such as those corresponding to the transmembrane action potential signals shown in FIGS. 12-15) may differ from the "normal" signals (such as those shown in FIG. 11) and may therefore determine that a condition such as Brugada syndrome is present in the mapped tissue. This determination may be communicated to the user, such as through one or more system displays 60, and the user may then initiate a treatment procedure to ablate or otherwise thermally and/or electrically affect the tissue identify as being affected by Brugada syndrome.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, the device comprising:
a distal assembly including:
an outer shell;
at least one inflatable element within the outer shell; and
an electrode assembly at least partially within the outer shell proximate the at least one inflatable element, the electrode assembly including;
a central shaft;
a plurality of carrier arms coupled to the central shaft; and
a plurality of electrodes, at least one of the plurality of electrodes being coupled to each of the plurality of carrier arms.

2. The device of claim 1, wherein the plurality of electrodes is a plurality of mapping electrodes.

3. The device of claim 1, wherein each of the plurality of carrier arms has a first end and a second end opposite the first end, the first end being coupled to the central shaft and the second end being coupled to the at least one of the plurality of electrodes.

4. The device of claim 3, wherein the second end of each of the plurality of carrier arms is coupled to at least two of the plurality of electrodes.

5. The device of claim 3, wherein the plurality of carrier arms includes a first set of carrier arms and a second set of carrier arms, the central shaft includes a first side and a second side, the first set of carrier arms being coupled to the first side of the central shaft and the second set of carrier arms being coupled to the second side of the central shaft.

6. The device of claim 5, wherein each carrier arm of the first set of carrier arms is at least substantially opposite a corresponding carrier arm of the second set of carrier arms.

7. The device of claim 5, wherein the first set of carrier arms alternates with the second set of carrier arms.

8. The device of claim 1, wherein the outer shell includes a first portion composed of a first material and a second portion composed of a second material.

9. The device of claim 8, wherein the first material is a semi-compliant material.

10. The device of claim 8, wherein the second material is a mesh.

11. The device of claim 8, wherein the at least one inflatable element is proximate the first portion and the electrode assembly is proximate the second portion.

12. The device of claim 8, wherein the outer shell includes an outer surface and an inner chamber, the central shaft and the plurality of carrier arms being located within the inner chamber of the outer shell and the plurality of electrodes at least partially extending from the outer surface of the outer shell second portion.

13. The device of claim 1, further comprising an elongate body including a distal portion, a proximal portion opposite the distal portion, and a lumen extending therebetween, the outer shell being coupled to the elongate body distal portion.

14. The device of claim 13, wherein each of the at least one inflatable element is in fluid communication with an inflation conduit located at least partially within the elongate body lumen.

15. The device of claim 1, further comprising:
a sheath including a distal portion, a proximal portion opposite the distal portion, and a lumen extending therebetween;
a retention element coupled to the sheath distal portion; and
a stopper located distal to the distal assembly, the stopper being engageable with the retention element and the distal assembly being retractable within the sheath.

16. The device of claim 15, wherein the retention element includes an annular element and at least one tether, each of the at least one tether having a first end coupled to the sheath distal portion and a second end coupled to the annular element, the stopper being engageable with the annular element when the distal assembly is retracted within the sheath lumen.

17. A mapping system, the system comprising:
an elongate body including a distal portion, a proximal portion opposite the distal portion, and a lumen extending therebetween;
an outer shell coupled to the distal portion of the elongate body, the outer shell having a first portion composed of a first material, a second portion composed of a second material, a proximal end, and a distal end;
at least one inflatable element within the outer shell and proximate the first portion of the outer shell;
an electrode assembly at least partially within the outer shell between the at least one inflatable element and the second portion of the outer shell, the electrode assembly having:
a central shaft at least partially disposed with the lumen of the elongate body;
a plurality of carrier arms, each of the plurality of carrier arms having a first end and a second end opposite the first end, the first end being coupled to the central shaft; and
a plurality of mapping electrodes, at least one of the plurality of mapping electrodes being coupled to the second end of each of the plurality of carrier arms;
a sheath including a distal portion, a proximal portion opposite the distal portion, and a lumen extending therebetween, the sheath being retractable within the distal portion of the elongate body;
a retention element coupled to the sheath distal portion; and
a stopper located distal to the distal end of the outer shell, the stopper being engageable with the retention element.

18. The system of claim 17, further comprising a control unit including processing circuitry configured to receive from the plurality of mapping electrodes mapping signals recorded from an area of tissue, the processing circuitry being programmed to:
compare the recorded mapping signals to mapping signals of healthy tissue; and
determine if the comparison indicates the presence of Brugada syndrome in the area of tissue.

* * * * *